(12) United States Patent
Van Der Borght et al.

(10) Patent No.: US 9,102,922 B2
(45) Date of Patent: Aug. 11, 2015

(54) TREHALOSE PHOSPHORYLASES AND THEIR USE IN THE BIOCATALYTIC PRODUCTION OF TREHALOSE-ANALOGUES AND GLYCOSYL PHOSPHATES

(75) Inventors: Jef Van Der Borght, Dikkelvenne (BE); Tom Desmet, Nevele (BE); Wim Soetaert, Lovendegem (BE); Chao Chen, Ghent (BE)

(73) Assignee: Universiteit Gent, Ghent (BE)

( * ) Notice: Subject to any disclaimer, the term of this patent is extended or adjusted under 35 U.S.C. 154(b) by 0 days.

(21) Appl. No.: 13/885,789

(22) PCT Filed: Dec. 9, 2011

(86) PCT No.: PCT/EP2011/072269
§ 371 (c)(1),
(2), (4) Date: May 16, 2013

(87) PCT Pub. No.: WO2012/080100
PCT Pub. Date: Jun. 21, 2012

(65) Prior Publication Data
US 2013/0302857 A1 Nov. 14, 2013

(30) Foreign Application Priority Data

Dec. 14, 2010 (EP) .................................... 10194958

(51) Int. Cl.
*C12N 9/10* (2006.01)
*C12P 19/12* (2006.01)
*C12P 19/18* (2006.01)
*C12P 19/02* (2006.01)

(52) U.S. Cl.
CPC .............. *C12N 9/1051* (2013.01); *C12P 19/02* (2013.01); *C12P 19/12* (2013.01); *C12P 19/18* (2013.01); *C12Y 204/01064* (2013.01)

(58) Field of Classification Search
CPC ......... C12C 7/04; C12P 19/18; C12N 9/1051; C12Y 204/01231

USPC ..................................................... 435/97, 193
See application file for complete search history.

(56) References Cited

U.S. PATENT DOCUMENTS 5,993,889 A 11/1999 Nakada et al.

OTHER PUBLICATIONS

Aisaka et al., "Enzymatic synthesis of novel disaccharides using disaccharide phosphorylases," J Biosci Bioeng. 90(2):208-213 (2000).
Accession No. B7R7E1. Retrieved on May 24, 2011 (1 page).
Accession No. DD917913. Retrieved on Apr. 19, 2011 (1 page).
Maruta et al., "Acceptor specificity of trehalose phosphorylase from *Thermoanaerobacter brockii*: Production of novel nonreducing trisaccharide, 6-O-α-D-galactopyranosyl trehalose," J Biosci Bioeng. 101(5):385-390 (2006).
Van der Borght et al., "Enzymatic properties and substrate specificity of the trehalose phosphorylase from *Caldanaerobacter subterraneus*," Appl Environ Microbiol. 77(19):6939-6944 (2011).
Yamamoto et al., "Construction and characterization of chimeric enzymes of kojibiose phosphorylase and trehalose phosphorylase from *Thermoanaerobacter brockii*," Carbohydr Res. 341(14):2350-2359 (2006).
International Preliminary Report on Patentability for International Application No. PCT/EP2011/072269, dated Jun. 18, 2013 (9 pages).
International Search Report for International Application No. PCT/EP2011/072269, mailed May 9, 2012 (6 pages).
Written Opinion for International Application No. PCT/EP2011/072269, mailed May 9, 2012 (8 pages).

*Primary Examiner* — David J Steadman
*Assistant Examiner* — Paul Holland
(74) *Attorney, Agent, or Firm* — Clark & Elbing LLP (57) ABSTRACT

The present invention relates to trehalose phosphorylases which are useful for the industrial production of trehalose-analogs and glycosyl phosphates. More specifically, the invention discloses trehalose phosphorylases which are mutated in specific amino acid regions. These specific mutations result in modified substrate specificities of the enzymes. In addition, the present invention discloses a wild type trehalose phosphorylase from the marine organism *Caldanaerobacter subterraneus*, and mutated types thereof, which are highly thermostable and have a broad acceptor and donor specificity.

9 Claims, 2 Drawing Sheets

TREHALOSE PHOSPHORYLASES AND THEIR USE IN THE BIOCATALYTIC PRODUCTION OF TREHALOSE-ANALOGUES AND GLYCOSYL PHOSPHATES

CROSS-REFERENCE TO RELATED APPLICATIONS

This application is the U.S. National Stage filing under 35 U.S.C. §371 of International Application No. PCT/EP2011/072269, filed Dec. 9, 2011, which claims the benefit of European Patent Application No. 10194958.4, filed Dec. 14, 2010.

TECHNICAL FIELD OF INVENTION

The present invention relates to trehalose phosphorylases which are useful for the industrial production of trehalose-analogues and glycosyl phosphates. More specifically, the invention discloses trehalose phosphorylases which are mutated in specific amino acid regions. These specific mutations result in modified substrate specificities of the enzymes. In addition, the present invention discloses a wild-type trehalose phosphorylase from the marine organism *Caldanaerobacter subterraneus*, and mutated types thereof, which are highly thermostable and have a broad acceptor and donor specificity.

BACKGROUND ART

Trehalose (glucose-α-1,1-α-glucose) is a non-reducing disaccharide with some very interesting properties (Higashiyama, 2002). It is present in a wide range of organisms (most notably yeast and plants), where it protects against environmental stresses such as heat, freezing and drought. It is also stable at a wide range of pH-values, has a mild sweet taste and is not cariogenic. These properties make it ideally suited for use in processed food. In the end, ingested trehalose is hydrolysed by intestinal trehalase (EC 3.2.1.28) and absorbed in the small intestine.

Trehalose is produced at an industrial scale from maltodextrins in a two-step process (Maruta et al, 1995). First, maltooligosyl trehalose synthase catalyses the conversion of the α-1,4-bond at the reducing end into an α-1,1-α-bond, after which the adjacent α-1,4-bond is hydrolysed by maltooligosyl trehalose trehalohydrolase to release trehalose. The industrial process was developed by Hayashibara and has allowed the production of trehalose at a very competitive price of a few €/kg (EP0606753 and EP0628630). However, the process can not be used for the production of trehalose-analogues that contain other monosaccharides than glucose.

Analogues of trehalose could have some additional benefits with respect to their physicochemical and biological properties. Galactose-α-1,1-α-glucose (hereafter referred to as lactotrehalose), for example, is not hydrolysed by intestinal trehalase but functions as a competitive inhibitor (Kim et al., 2007). This means that this disaccharide does not contribute to the caloric content of food preparations and also lowers the metabolic conversion of trehalose. Unfortunately, trehalose-analogues are not yet produced at an industrial scale and have, therefore, not been studied very extensively.

The chemical synthesis of trehalose-analogues has been described several years ago (Youssef et al., 1995; Lee et al., 1976, Pratt et al., 2003). However, these procedures consist of multistep synthetic routes that have a low overall yield and generate a lot of waste. Alternatively, a glucosyltransferase has been described that catalyses the synthesis of lactotrehalose from UDP-glucose and galactose (Kim et al., 2007). Although very efficient, the need for an expensive nucleotide-activated donor prohibits the cost-efficient exploitation of this enzyme. Furthermore, other acceptors besides galactose can not be used, restricting its application to the synthesis of lactotrehalose.

Finally, the synthesis of trehalose-analogues has also been described for trehalose phosphorylase (Belocopitow et al., 1971; Aisaka et al., 2000; Chaen et al., 2001). This enzyme normally catalyses the degradation of trehalose into β-glucose-1-phosphate and D-glucose, but the reaction can also be run in the synthetic direction. In that case, a glucosyl phosphate is required as donor, which is much cheaper and more stable then a nucleotide-activated donor. Activity of trehalose phosphorylases on D-glucosamine, D-xylose, D-galactose, D-fucose, L-fucose and L-arabinose as acceptors has been reported, albeit at a reduced rate (Chaen et al. 1999). In addition, oligosaccharides with a reducing-end glucose residue are successful acceptors for the trehalose phosphorylase from *Thermoanaerobacter brockii* ATCC 35047 (Maruta et al., 2006). Chimeric phosphorylases have been created that combine parts of the kojibiose phosphorylase and of the trehalose phosphorylase from *Thermoanaerobacter brockii* (Yamamoto et al., 2006). Although the resulting enzymes have altered substrate specificities, they do not display activity towards new acceptors. U.S. Pat. No. 5,993,889 also discloses a trehalose phosphorylase obtainable from microorganisms of the genus *Thermoanaerobium* which can be used to synthesize trehalose-analogues and further indicates that functional equivalents of the enzyme can be obtained by treating the microorganisms with an appropriate mutagen. However, this document does not teach which specific mutation(s) will result in beneficial and useful properties of the enzyme and which specific mutation(s) will result in detrimental or useless properties of the enzymes.

There is thus still a need within industry to have access to alternative trehalose phosphorylases which are highly thermostable, have a broad acceptor specificity and have a high activity on the acceptors. Such trehalose phosphorylases are useful for the industrial production of trehalose-analogues. Trehalose phosphorylases having an optimized donor specificity are useful for the production of glycosyl phosphates.

SUMMARY OF THE INVENTION

The present invention provides the following embodiments:

1. A mutated trehalose phosphorylase containing at least one mutation in the amino acid positions 371, 442, 450, 649, 659 or 693 wherein said amino acid positions correspond to the amino acid positions as determined by SEQ ID N° 1 or to corresponding amino acid positions in a trehalose phosphorylase having an amino acid sequence which is at least 75% identical to SEQ ID N° 1, and wherein said mutated trehalose phosphorylase has an increased catalytic efficiency towards its acceptor or donor substrate compared to the corresponding wild-type trehalose phosphorylase.
2. The mutated trehalose phosphorylase according to embodiment 1 wherein said mutation is a substitution at amino acid positions 371, 442, 450, 649, 659 and 693 of SEQ ID N° 1 or at corresponding amino acid positions in a trehalose phosphorylase having an amino acid sequence which is at least 75% identical to SEQ ID N° 1.
3. Use of a polypeptide having the amino acid sequence as depicted by SEQ ID N° 1 as a trehalose phosphorylase, wherein said trehalose phosphorylase has a relative activity of at least 80% on the acceptors D-glucose, D-xylose, L-arabinose, L-fucose and/or D-galactose, or, of a variant thereof having a sequence identity of at least 90% with SEQ ID N° 1 and having a relative activity of at least 80% on the acceptors D-glucose, D-xylose, L-arabinose L-fucose and/or D-galactose, or, of a fragment thereof having a relative activity of at least 80% on the acceptors D-glucose, D-xylose, L-arabinose, L-fucose and/or D-galactose.
4. Use according to embodiment 3, whereby said polypeptide is isolated from *Caldanaerobacter subterraneus*
5. Use according to any one of embodiments 3 to 4 wherein said polypeptide is encoded by a nucleotide sequence as depicted by SEQ ID N° 2 or SEQ ID N° 3.
6. A variant according to any one of embodiments 3 to 5, characterized in that said variant has a mutation in the amino acid regions 420-480 or 580-670 of SEQ ID N° 1.
7. A variant according embodiment 6 characterized in that said variant has a mutation at amino acid positions 442, 450 or 659 of SEQ ID N° 1.
8. A fragment according to any one of embodiments 3 to 5 or a fragment of a variant according to any one of embodiments 6 to 7 having a relative activity of at least 80% on the acceptors D-glucose, D-xylose, L-arabinose, L-fucose and/or D-galactose.
9. A fragment according to any one of embodiments 3 to 5 characterized in that said fragment comprises the amino acid regions 420-480 or 580-670 of SEQ ID N° 1.
10. A fragment according to embodiment 9 characterized in that said fragment comprises the amino acid positions 442, 450 or 659 of SEQ ID N° 1.
11. A mutated trehalose phosphorylase according to embodiment 1 or 2 or a variant or fragment according to any one of embodiments 6 to 10 which is recombinantly expressed in a host cell.
12. Use of mutated trehalose phosphorylase according to embodiment 1 or 2, or of a variant or fragment according to any one of embodiments 6 to 10, or of a trehalose phosphorylase as described in any one of embodiments 3 to 5 for the production of trehalose-analogues.
13. Use according to embodiment 12 wherein said trehalose-analogue is galactose-alpha-1,1-alpha-glucose.
14. A method to produce trehalose-analogues comprising:
    contacting a mutated trehalose phosphorylase according to embodiment 1 or 2, or a variant or fragment thereof according to any one of embodiments 6 to 10, or of a trehalose phosphorylase as described in any one of embodiments 3 to 5 with β-glucose-1-phosphate and a monosaccharide,
    glycosylating said monosaccharide to obtain a trehalose-analogue, and
    purifying said trehalose-analogue.
15. A method to produce trehalose-analogues comprising:
    contacting a mutated trehalose phosphorylase according to embodiment 1 or 2, or a variant or fragment thereof according to any one of embodiments 6 to 10, or of a trehalose phosphorylase as described in any one of embodiments 3 to 5 with trehalose and a monosaccharide in phosphate buffer,
    glycosylating said monosaccharide to obtain a trehalose-analogue, and
    purifying said trehalose-analogue.
16. A method according to embodiment 14 or 15 wherein said monosaccharide is chosen from the group consisting of D-glucose, D-xylose, L-arabinose, L-fucose and D-galactose.
17. A variant trehalose phosphorylase characterized in having the amino acid sequence as depicted by SEQ ID N° 1 but having at least one mutation in the amino acid regions 330-410 or 630-710 so that, compared to the wild type enzyme, said variant displays a significant increase in the ratio of beta-galactose-1-phosphate over beta-glucose-1-phosphate release from lactotrehalose
18. A variant according to embodiment 17 further characterized in that said variant has a mutation in the amino acid positions 649, or 649 and 693, or 649 and 693 and 371.
19. A fragment of a variant according to embodiment 17 or 18 which comprises the amino acid regions 330-410 or 630-710 and displays a significant increase in the ratio of beta-galactose-1-phosphate over beta-glucose-1-phosphate release from lactotrehalose.
20. A method to produce a glycosyl phosphate comprising:
    generating a variant trehalose phosphorylase or fragment thereof with increased acceptor specificity for a monosaccharide such as D-xylose, L-arabinose, L-fucose or D-galactose,
    contacting said mutant or variant trehalose phosphorylase with said monosaccharide and β-glucose-1-phosphate to generate a corresponding trehalose-analogue,
    generating a mutant or variant trehalose phosphorylase with increased donor specificity for said trehalose-analogue,
    contacting said mutant or variant trehalose phosphorylase with increased donor specificity for said trehalose-analogue with said trehalose-analogue in phosphate buffer,
    allowing the production of a glycosyl phosphate comprising said monosaccharide and a phosphate group, and
    purifying said glycosyl phosphate.
21. A method to produce β-galactose-1-phosphate comprising:
    contacting a variant trehalose phosphorylase or a fragment thereof according to any one of embodiments 17 to 19 with lactotrehalose in phosphate buffer,
    allowing the production of β-galactose-1-phosphate, and
    purifying said β-galactose-1-phosphate.

DESCRIPTION OF INVENTION

The present invention provides alternative trehalose phosphorylases which are useful for the industrial production of trehalose-analogues and/or glycosyl phosphates. More specifically, the invention discloses trehalose phosphorylases (TP) which are mutated in specific amino acid regions. Said specific mutations result in modified and useful substrate specificities of the enzymes.

The present invention thus relates to a mutated trehalose phosphorylase containing at least one mutation in the amino acid positions 371, 442, 450, 649, 659 or 693, wherein said amino acid positions correspond to the amino acid positions as determined by SEQ ID N° 1 or to a corresponding amino acid position in a trehalose phosphorylase having an amino acid sequence which is at least 75% identical to SEQ ID N° 1, and wherein said mutated trehalose phosphorylase displays an increased catalytic efficiency towards its acceptor or donor substrate compared to the corresponding wild-type trehalose phosphorylase.

The term 'mutated trehalose phosphorylase' relates to a 'modified' wild-type trehalose phosphorylase obtainable from the marine organism *Carboxydibrachium pacificum* and having the amino acid sequence as depicted by SEQ ID N° 1, or, relates to a 'modified' homologue of said sequence. The term 'modified' indicates that there is at least one amino acid which is absent compared to SEQ ID N° 1 and/or there is at least one amino acid which is different compared to SEQ ID N° 1 and/or there is at least one amino acid which is additional compared to SEQ ID N° 1. Multiple modifications or combinations of several different modifications are also part of the present invention. Said modifications occur within specific regions of SEQ ID N° 1, namely the amino acid regions 330-480 and/or 580-710 as determined by SEQ ID N° 1. Specific, but non-limiting, examples of such mutated trehalose phosphorylases are given further. The term 'mutated' or 'mutation' refers to a spontaneous mutation and/or to an induced mutation in the nucleic acids encoding for the enzymes of the present invention. Said mutation can be a point mutation, deletion, insertion or any other type of mutation. A mutation as used here can actually be obtained by any method known to the person skilled in the art. Specific, but non-limiting, methods used in the present invention are site-saturation mutagenesis with degenerate primers (NNK) as described by Sanchis et al. (2008) and random mutagenesis performed with the GeneMorph II EZClone Domain Mutagenesis Kit (Stratagene) according to the manufacturer's instructions. The term 'a homologue of said sequence' relates to a trehalose phosphorylase having at least a sequence identity of 75% with SEQ ID N° 1. Hence, said sequence identity can be 75, 76, 77, 78, 79, 80, 81, 82, 83, 84, 85, 86, 87, 88, 89, 90, 91, 92, 93, 94, 95, 96, 97, 98 or 99%. A skilled person can easily determine the identity of a particular sequence with SEQ ID N° 1 via aligning both sequences. In analogy, a skilled person can easily define corresponding amino acids or amino acid regions within both sequences as defined by the present invention via aligning both sequences.

The term 'an increased catalytic efficiency towards its acceptor or donor substrate compared to the corresponding wild-type trehalose phosphorylase' relates in essence to specific mutations within specific regions as defined above which result in beneficial and useful properties of the enzyme. Said beneficial and useful properties of the enzymes of the present invention relate—for example—to an increased efficiency towards a specific substrate, acceptor or donor. More specific—but non-limiting examples—of modified activities are: 1) the substitution of the lysine residue at position 450 of SEQ ID N° 1 for a serine which results in a two-fold increase in catalytic efficiency (as measured by $k_{cat}/K_m$) on 30 mM galactose as acceptor or the substitution K450N which significantly increases the enzyme's specific activity on mannose as acceptor, 2) mutagenesis of residue Ala442 of SEQ ID N° 1 into Val442 also results in a two-fold increase in activity (as measured by $k_{cat}/K_m$) on galactose as acceptor, 3) mutagenesis at position 659 of SEQ ID N° 1 (N659Y) also results in a two-fold increase in activity (as measured by $k_{cat}/K_m$) on galactose as acceptor. These beneficial mutations can also be combined, e.g. A442V/K450S/N659Y, to create an enzyme that is even more efficient towards galactose as acceptor, 4) the substitution of the leucine residue at position 649 of SEQ ID N° 1 for a glycine which results in a 60-fold increase in the ratio of beta-galactose-1-phosphate over beta-glucose-1-phosphate release from lactotrehalose, 5) the addition of mutation A693Q to the variant L649G further increases this ratio 9-fold, 6) the addition of mutation W371Y A to the variant L649G/A693Q further increases this ratio 4-fold.

Hence, the present invention more specifically relates to a mutated trehalose phosphorylase as indicated above wherein said mutation is a substitution at amino acid positions 371, 442, 450, 649, 659 or 693 of SEQ ID N° 1 or at corresponding amino acid positions in a trehalose phosphorylase having an amino acid sequence which is at least 75% identical to SEQ ID N° 1. Non-limiting examples of 'corresponding amino acid positions in a trehalose phosphorylase having an amino acid sequence which is at least 75% identical to SEQ ID N° 1' are the positions 369, 440, 448, 647, 657 or 691 in the trehalose phosphorylase of *T. brockii* as disclosed by U.S. Pat. No. 5,993,889. Indeed, for example the substitutions A440V, R448S and N657Y, or combinations thereof, increase the efficiency of the enzyme towards galactose as acceptor.

In addition, the present invention discloses the usage of a wild-type trehalose phosphorylase from the marine organism *Caldanaerobacter subterraneus*, and mutated types thereof, which are highly thermostable and have a broad acceptor specificity.

In other words, said trehalose phosphorylases are useful for the industrial production of trehalose-analogues. Indeed the present invention discloses the cloning and characterization of a trehalose phosphorylase from *Carboxydibrachium pacificum* with surprising characteristics:
1) the enzyme is highly thermostable as it, for example, retains 100% of its activity after 1 hour incubation at 65° C., and
2) the enzyme displays high activity: i.e. having a relative activity on, at least, the acceptors D-glucose, D-xylose, L-arabinose, L-fucose and/or D-galactose which is equal to—or greater than 80%

It was also for this enzyme found that amino acids which define the acceptor specificity of the trehalose phosphorylase reside in the amino acids regions 420-480 and 580-670 of the 783 amino acid sequence (depicted by SEQ ID N° 1) of said trehalose phosphorylase. The donor specificity of this enzyme resides in the amino acid regions 330-410 and 630-710.

Hence, it is a further aspect of the present invention to provide the usage of a trehalose phosphorylase having the amino acid sequence as depicted by SEQ ID N° 1 and having a relative activity on the acceptors D-glucose, D-xylose, L-arabinose, L-fucose and/or D-galactose which is equal to—or greater than 80%, or of a variant thereof having a sequence identity of at least 90% with SEQ ID N° 1 and having a relative activity on the acceptors D-glucose, D-xylose, L-arabinose, L-fucose and/or D-galactose which is equal to—or greater than 80%, or of a fragment thereof having a relative activity on the acceptors D-glucose, D-xylose, L-arabinose, L-fucose and/or D-galactose which is equal to—or greater than 80%.

The term "variant" refers to an enzyme having at least 90% sequence identity, i.e. having 90, 91, 92, 93, 94, 95, 96, 97, 98, 99 or 100% sequence identity with SEQ ID N° 1, and, and having relative activity of at least 80% on the acceptors D-glucose, D-xylose, L-arabinose, L-fucose and/or D-galactose. Hence, the usage of orthologues, or genes in other genera and species (than the genus *Caldanaerobacter* or the species *Caldanaerobacter subterraneus*) with at least 90% identity percentage identity at amino acid level, and having the described function is part of the present invention. The percentage of amino acid sequence identity is determined by alignment of the two sequences and identification of the number of positions with identical amino acids divided by the number of amino acids in the shorter of the sequences×100. The latter 'variant' may also differ from the protein as depicted by SEQ ID N° 1 only in conservative substitutions and/or modifications, such that the ability of the protein to have trehalose phosphorylase activity is retained, i.e. said protein has a relative activity of at least 80% on the acceptors D-glucose, D-xylose, L-arabinose, L-fucose and/or D-galactose. A "conservative substitution" is one in which an amino acid is substituted for another amino acid that has similar properties, such that one skilled in the art of protein chemistry would expect the nature of the protein to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

Variants may also (or alternatively) be proteins as described herein modified, for example, by the deletion or addition of amino acids that have minimal influence on the trehalose phosphorylase activity as defined above, secondary structure and hydropathic nature of the enzyme. Regions within SEQ ID N° 1 which contribute to the proteins' activity are the amino acid regions 330-480 and 580-710 of SEQ ID N° 1. Hence, the variants as defined above preferably comprise at least one of the latter regions and are part of the present invention. More specifically, said variants according to the present invention comprise at least one of the residues corresponding to the amino acid positions 371, 442, 450, 649, 659 or 693 of SEQ ID N° 1.

The term 'fragment' refers to a protein containing fewer amino acids than the amino acid sequence as depicted by SEQ ID N° 1 and that retains trehalose phosphorylase activity, i.e. having relative activity of at least 80% on the acceptors D-glucose, D-xylose, L-arabinose, L-fucose and/or D-galactose. Specific fragments of the present invention comprise at least the amino acid regions 330-480 and 580-710 of SEQ ID N° 1, and, more specifically, comprise at least one of the amino acid positions 371, 442, 450, 649, 659 or 693 of SEQ ID N° 1.

Hence, the invention thus also relates to 'a fragment of a variant' as described above having a relative activity of at least 80% on the acceptors D-glucose, D-xylose, L-arabinose, L-fucose and/or D-galactose, and, relates to 'a fragment' as described above characterized in that said fragment comprises at least one of the amino acid regions 330-480 and 580-710 of SEQ ID N° 1. More specifically, the present invention relates to a fragment as described above characterized in that said fragment comprises at least one of the amino acid positions 371, 442, 450, 649, 659 or 693 of SEQ ID N° 1.

The term 'relative activity' as used in the terms 'having a relative activity on the acceptors D-glucose, D-xylose, L-arabinose, L-fucose and/or D-galactose which is equal to—or greater than 80%' reflects the percentage activity of the enzyme on the acceptors compared to the activity of the enzyme on its normal substrate or acceptor, i.e. D-glucose, which is equal to 100%, and when the substrate/acceptor is present at saturating concentrations. The substrates or acceptors of the present invention comprise at least D-glucose, D-xylose, L-arabinose, L-fucose and/or D-galactose and the relative activity on these acceptors is 80, 85, 90, 95, 100, 105, 110, 115, 120, 125, 130, 135, 140, 145, 150 or greater than 150%. The maximum efficiency of the enzymes of the present invention occurs at a pH of about 7 (i.e. between 6 and 8) and at a temperature of about 80° C. (i.e. between 60 and 90° C.).

The invention further, and more specifically, relates to the usage of a trehalose phosphorylase enzyme as described above, whereby said enzyme is isolated from *Caldanaerobacter subterraneus*. The sequence depicted by SEQ ID N° 1 corresponds to a trehalose phosphorylase isolated from *Caldanaerobacter subterraneus*. *Caldanaerobacter subterraneus* relates to a bacterium species which was previously known as *Carboxydibrachium pacificum* (Sokolova et al., 2001; Fardeau et al., 2004). More specifically, the present invention relates to the species—and its genome—*Carboxydibrachium pacificum* DSM 12653.

The invention further relates to the usage of a nucleotide sequence encoding for a trehalose phosphorylase as described above.

More specifically, the present invention relates to the usage of nucleotide sequences encoding for a polypeptide (=a trehalose phosphorylase) whereby said sequences have the nucleotide sequence as depicted by SEQ ID N° 2 or SEQ ID N° 3:

```
A/ gene sequence of a trehalose phosphorylase in genome of
Caldanaerobacter subterraneus
                                                            (SEQ ID N°2)
ATGGATATGGTGAAAAAGACGAAGAAGCCCATTTACCCTTTTGAAGATTGGACAATAAGGGAGACA

GAGTTTAGCATAGAAACAAACTATAGAAATGAGACAATTTTTGCTCAGGCGAATGGATATATGGGA

ATGAGAGGAAATTTTGAAGAAGGGTATTCAGGACCTGACGGTACTTCCTTAAAAGGGACTTATATT

AATGGGTTTTATGAAATACACGATATCATCTACCCTGAAGGGGGATACGGTTTTGCGAAAACAGGG

CAGACCATGTTAAATGTGGCTGACAGCAAAATAATAGAATTGTACGTAGGAGAAGAAAAATTTGAC

CTTTTAAAAGGTAAAATCCACTTTTATGAAAGAGTACTTGATATGAAAAAAGGTTGTGTAGAAAGA

AAGATAAAGTGGGAGTCTCCTTCAGGAAAGATTGTAAATGTAAAAATAAAGAGAATTGTTTCATTG

CAAAGGCAACATTTAGCAGTAATTTCTTTTTCTGTAGAACCTGTTAATTTTACGGGAAATATAAAA

TTTGTATCTGCTATTGATGGAGATGTGAGGAACATTACTGAGAGCGAAGATGTAAGAGTGGGTTCA

AATCTGAAGGGGAGAGTTTTAGAGACCGTCGAAAGAGGAACAAATGGCTTTGAGGGATGGATTTCT

CAAAAAACACAAAAAAGCAACCTTTCATATACTTGCGCAATGAAAAATGAACTCATTGGGACAGAA

AAATACGAGGTTTTGAACAACGTAAAAGAAGATAGGGTAGAGGTTGCAGTAGCTTTTAAAGCTGAG
```

-continued

AAGAATAGGGTATACATTCTGAATAAATTTATATCTTATTATACCTCAAAAGATTGCGACAAAAGT

GAAACAATGAAATTGGCCTTAGAAGAAGTGAGAAGAGCACAAGAAGATGGATTTTGCAAATAGAA

AAAGAGCAGGAAGAATTTTTGCAATCTTTCTGGGAAGATGCCGATGTAGTAATAGAAGGAGATAAG

GCTCTGCAGCAGGGTATAAGATTTAATATGTTTCACCTTTTGCAGTCTGTCGGTAGAGACGGAAAA

ACTAATATTGCGGCAAAGGGACTTACTGGGGAAGGGTATGAAGGCCATTACTTTTGGGATTCTGAT

ATCTATATATTGCCTTTTTTCCTTTACACGAAGCCAGAAATTGCAAAAGCTTTAATAATGTATAGA

TATAACCTCTTAGATGCTGCGAGAAATAGGGCTAAAGAGTTGGGGCATAAAGGAGCTTTATACCCC

TGGAGGACAATTGATGGACCTGAATGTTCTGCATACTTTCCTGCTGGAACTGCTCAATATCACATA

AATGCTGATATAGTTTATGCTTTAAAAAAGTATGTGGAGGCCACGAATGATTTGGATTTTCTCTAT

GACTACGGCTGTGAAATAGTATTTGAAACTGCAAGGTTTTGGGAAGATTTAGGAGCATATATTCCT

CTTAAAGGAAATAAATTCTGTATAAACACTGTCACTGGTCCTGATGAGTATACGGCATTGGTTGAT

AATAACGCATATACAAATTATATGGCAAAAATGAATTTGGAATACGCCTATGATATTGCAAACAAA

ATGAAAAAGGAAGTGCCTGAAAAGTATCAAAAGGTCGCTTCAAAACTAAATCTAAAGGATGAAGAG

ATTGCTTCGTGGAAAAGGGCAGCTAACAATATGTACCTTCCTTACTCGGAAGAGCTTGATATTATA

CCACAGGATGACAGTTTTTTGTATAAAGAAAGGATAACAGTGGATGAAATACCGGAAGATCAATTT

CCGTTATTGCTTCACTGGCACTACCTCAACATTTACAGGTATCAGATCTGCAAACAGCCTGATGTG

TTGCTTTTGATGTTTTTACAGAGAGAAAAATTTACTATAGAACAGCTTAAAAAGAATTTTGATTAT

TATGAACCTATTACTACTCACGACTCTTCCCTGTCGCCAGCAATATTTAGTATACTTGCCAATGAA

ATAGGGTATACTGACAAAGCTTATAAATACTTTATGATGACTGCAAGGATGGACTTGGATGATTAC

AATGACAATGTAAAAGATGGAATTCATGCTGCAGCAATGGCAGGGTCCTGGAGTGCCGTTGTAAAT

GGTTTTGGAGGAATGAGAGTTTATACAGATGAACTGCACTTTACTCCAGGACTGCCTGAGGGGTGG

AAGATGCTCTCTTTTAATGTAAAGTACAAAGGGAGGAAGATAAATGTAAAATTAACTCATGAAGAA

TCAGTATTTACCCTTTTGGAAGGAGAACCTATAGAAATTTTCTATTTTGACAGAAGAGTGTTAATA

AAGTCAGGAGAAAATATACTAAAAGGGTATGAGGAGAAGTGA

B/ Codon-optimized gene sequence of Caldanaerobacter subterraneus
for optimal expression in E. coli
(SEQ ID N°3)
ATGGACATGGTTAAAAAAACCAAAAAACCGATCTACCCGTTCGAAGACTGGACCATCCGTGAAACC

GAATTCTCTATCGAAACCAACTACCGTAACGAAACCATCTTCGCTCAGGCTAACGGTTACATGGGT

ATGCGTGGTAACTTCGAAGAAGGTTACTCTGGTCCGGACGGTACCTCTCTGAAAGGTACCTACATC

AACGGTTTCTACGAAATCCACGACATCATCTACCCGGAAGGTGGTTACGGTTTCGCTAAAACCGGT

CAGACCATGCTGAACGTTGCTGACTCTAAAATCATCGAACTGTACGTTGGTGAAGAAAAATTCGAC

CTGCTGAAAGGTAAAATCCACTTCTACGAACGTGTTCTGGACATGAAAAAAGGTTGCGTTGAACGT

AAAATCAAATGGGAATCTCCGTCTGGTAAAATCGTTAACGTTAAAATCAAACGTATCGTTTCTCTG

CAGCGTCAGCACCTGGCTGTTATCTCTTTCTCTGTTGAACCGGTTAACTTCACCGGTAACATCAAA

TTCGTTTCTGCTATCGACGGTGACGTTCGTAACATCACCGAATCTGAAGACGTTCGTGTTGGTTCT

AACCTGAAAGGTCGTGTTCTGGAAACCGTTGAACGTGGTACCAACGGTTTCGAAGGTTGGATCTCT

CAGAAAACCCAGAAATCTAACCTGTCTTACACCTGCGCTATGAAAAACGAACTGATCGGTACCGAA

AAATACGAAGTTCTGAACAACGTTAAAGAAGACCGTGTTGAAGTTGCTGTTGCTTTCAAAGCTGAA

AAAACCGTGTTTACATCCTGAACAAATTCATCTCTTACTACACCTCTAAAGACTGCGACAAATCT

GAAACCATGAAACTGGCTCTGGAAGAAGTTCGTCGTGCTCAGGAAGACGGTTTCTGCAAAATCGAA

AAAGAACAGGAAGAATTCCTGCAGTCTTTCTGGGAAGACGCTGACGTTGTTATCGAAGGTGACAAA

-continued
```
GCTCTGCAGCAGGGTATCCGTTTCAACATGTTCCACCTGCTGCAGTCTGTTGGTCGTGACGGTAAA

ACCAACATCGCTGCTAAAGGTCTGACCGGTGAAGGTTACGAAGGTCACTACTTCTGGGACTCTGAC

ATCTACATCCTGCCGTTCTTCCTGTACACCAAACCGGAAATCGCTAAAGCTCTGATCATGTACCGT

TACAACCTGCTGGACGCTGCTCGTAACCGTGCTAAAGAACTGGGTCACAAAGGTGCTCTGTACCCG

TGGCGTACCATCGACGGTCCGGAATGCTCTGCTTACTTCCCGGCTGGTACCGCTCAGTACCACATC

AACGCTGACATCGTTTACGCTCTGAAAAAATACGTTGAAGCTACCAACGACCTGGACTTCCTGTAC

GACTACGGTTGCGAAATCGTTTTCGAAACCGCTCGTTTCTGGGAAGACCTGGGTGCTTACATCCCG

CTGAAAGGTAACAAATTCTGCATCAACACCGTTACCGGTCCGGACGAATACACCGCTCTGGTTGAC

AACAACGCTTACACCAACTACATGGCTAAAATGAACCTGGAATACGCTTACGACATCGCTAACAAA

ATGAAAAAAGAAGTTCCGGAAAAATACCAGAAAGTTGCTTCTAAACTGAACCTGAAAGACGAAGAA

ATCGCTTCTTGGAAACGTGCTGCTAACAACATGTACCTGCCGTACTCTGAAGAACTGGACATCATC

CCGCAGGACGACTCTTTCCTGTACAAAGAACGTATCACCGTTGACGAAATCCCGGAAGACCAGTTC

CCGCTGCTGCTGCACTGGCACTACCTGAACATCTACCGTTACCAGATCTGCAAACAGCCGGACGTT

CTGCTGCTGATGTTCCTGCAGCGTGAAAAATTCACCATCGAACAGCTGAAAAAAAACTTCGACTAC

TACGAACCGATCACCACCCACGACTCTTCTCTGTCTCCGGCTATCTTCTCTATCCTGGCTAACGAA

ATCGGTTACACCGACAAAGCTTACAAATACTTCATGATGACCGCTCGTATGGACCTGGACGACTAC

AACGACAACGTTAAAGACGGTATCCACGCTGCTGCTATGGCTGGTTCTTGGTCTGCTGTTGTTAAC

GGTTTCGGTGGTATGCGTGTTTACACCGACGAACTGCACTTCACCCCGGGTCTGCCGGAAGGTTGG

AAAATGCTGTCTTTCAACGTTAAATACAAAGGTCGTAAAATCAACGTTAAACTGACCCACGAAGAA

TCTGTTTTCACCCTGCTGGAAGGTGAACCGATCGAAATCTTCTACTTCGACCGTCGTGTTCTGATC

AAATCTGGTGAAAACATCCTGAAAGGTTACGAAGAAAATAA
```

It is a further specific aspect of the present invention to provide for a mutant trehalose phosphorylase as described above, or, for a novel variant or fragment derived from SEQ ID N° 1 as described above, which is recombinantly expressed in a host cell. Said trehalose phosphorylase can thus be synthesized by using nucleic acid molecules which encode the enzymes of the present invention as described above in an appropriate expression vector which include the encoding nucleotide sequences. Such DNA molecules may be readily prepared using an automated DNA synthesizer and the well-known codon-amino acid relationship of the genetic code. Such a DNA molecule also may be obtained as genomic DNA or as cDNA using oligonucleotide probes and conventional hybridization methodologies. Such DNA molecules may be incorporated into expression vectors, including plasmids, which are adapted for the expression of the DNA and production of the enzymes in a suitable host such as a bacterium, yeast cell, animal cell or plant cell.

The present invention further relates to the usage of any trehalose phosphorylase as described above for the production of trehalose-analogues and specifically for the production of lactotrehalose (=galactose-alpha-1,1-alpha-glucose).

Hence, and more specifically, the present invention relates to the usage as described above wherein said trehalose-analogue is galactose-alpha-1,1-alpha-glucose (or glycosylgalactose (lactotrehalose)). Other non-limiting examples of trehalose-analogues are glycosylarabinose, glycosylxylose and glycosylfucose.

The present invention thus relates to a method to produce trehalose-analogues comprising:
  contacting any trehalose phosphorylase as described above (=a mutated trehalose phosphorylase which is at least 75% identical to SEQ ID N° 1 or a trehalose phosphorylase having the amino acid sequence as depicted by SEQ ID N° 1 or a variant or fragment thereof) with β-glucose-1-phosphate (as a required donor) and a monosaccharide (the acceptor),
  glycosylating said monosaccharide (in order to obtain a trehalose analogue), and
  purifying said trehalose analogue if necessary.

The present invention also relates to a method to produce trehalose-analogues comprising:
  contacting any trehalose phosphorylase as described above with trehalose and a monosaccharide in phosphate buffer in order to obtain a mixture of β-glucose-1-phosphate and a monosaccharide,
  glycosylating said monosaccharide to obtain a trehalose-analogue, and
  purifying said trehalose-analogue.

More specifically, the present invention relates to a method as described above wherein said monosaccharide is chosen from the group consisting of D-glucose, D-xylose, L-arabinose, L-fucose and D-galactose. The present invention further relates to mutated trehalose phosphorylases characterized in having the amino acid sequence as depicted by SEQ ID N° 1 but having at least one mutation in the amino acid region 330-410 and/or 630-710, and more specifically in the amino acid positions 371 and/or 649 and/or 693. The latter mutated trehalose phosphorylases have an optimized donor specificity. For example, and compared to the wild-type enzymes, these enzymes will preferentially produce beta-galactose-1-phosphate, and not beta-glucose-1-phosphate, from lactotrehalose as a substrate. Hence, the present invention relates to a variant trehalose phosphorylase, characterized in that said variant, compared to the wild type enzyme, displays a significant increase in the ratio of beta-galactose-1-phosphate over beta-glucose-1-phosphate release from lactotrehalose. The latter can be conveniently evaluated by the phosphorolysis of lactotrehalose. The present invention thus further relates to a variant as described above which is further characterized in that said variant has a mutation in the amino acid positions 649, or 649 and 693, or 649 and 693 and 371. The present invention further relates to a fragment of said variant which comprises a mutation in the amino acid positions 649, or 649 and 693, or 649 and 693 and 371.

In another aspect, the present invention also relates to a method to produce a glycosyl phosphate comprising:
- generating a variant trehalose phosphorylase or a fragment thereof with increased acceptor specificity for a monosaccharide such as D-xylose, L-arabinose, L-fucose or D-galactose as is indicated above,
- contacting said mutant or variant trehalose phosphorylase with said monosaccharide and β-glucose-1-phosphate to generate a corresponding trehalose-analogue,
- generating a mutant or variant trehalose phosphorylase with increased donor specificity for said trehalose-analogue as indicated above,
- contacting said mutant or variant trehalose phosphorylase with increased donor specificity for said trehalose-analogue with said trehalose-analogue in phosphate buffer,
- allowing the production of a glycosyl phosphate comprising said monosaccharide and a phosphate group, and
- purifying said glycosyl phosphate.

More specifically, the present invention relates to a method to produce β-galactose-1-phosphate comprising:
- contacting a variant trehalose phosphorylase or a fragment thereof as defined above with lactotrehalose in phosphate buffer,
- allowing the production of β-galactose-1-phosphate, and
- purifying said β-galactose-1-phosphate.

The present invention will now be illustrated by the following non-limiting examples.

EXAMPLES

Materials and Methods

The TP gene sequence was identified in the genome of *Carboxydibrachium pacificum* DSM 12653 (Accession number ZP_05091985), and optimized for expression in *E. coli* with the program JCat. The gene was chemically synthesized by Genscript. In contrast, the gene coding for the TP from *Thermoanaerobacter brookii* (Maruta et al., 2002) was amplified from the genomic DNA of strain DSMZ 1457 by PCR. The gene was cloned into the constitutive expression vector pCXP34h (Aerts et al., 2010), which adds a N-terminal (His)$_6$-tag to the enzyme. The resulting plasmid was transformed into *E. coli* XL-10 Gold (Stratagene), which was grown for 8 h at 37° C. to produce the enzyme. After chemoenzymatic cell lysis (Eayslyse, Epicentre), the His-tagged enzyme was purified by affinity chromatography using a Ni-NTA resin (Qiagen).

The phosphorolytic activity of the enzyme was determined using a discontinuous assay in which the released glucose is converted by glucose oxidase and peroxidase (GOD-POD) (Werner et al., 1970). The activity was assayed in 30 mM phosphate buffer at pH 7 and 60° C., using 30 mM disaccharide as substrate. The synthetic activity of the enzyme was determined using a discontinuous assay in which the released phosphate is complexed by molybdate and ascorbic acid (Gawronski and Benson, 2004). The activity was assayed in 50 mM MES buffer at pH 6 and 60° C., using 30 mM β-glucose-1-phosphate as donor and 500 mM of acceptor substrates. Because strong substrate inhibition was observed at a glucose concentration of 500 mM, this acceptor was used at a concentration of only 30 mM.

Site-saturation mutagenesis was performed with degenerate primers (NNK) as described by Sanchis et al. (2008), and random mutagenesis was performed with the GeneMorph II EZClone Domain Mutagenesis Kit (Stratagene) according to the manufacturer's instructions. The resulting DNA libraries were transformed into *E. coli* XL10-Gold, after which the cells were grown on solid LB medium in a Petri dish. Colonies were then transferred to 96-well microtiter plates containing liquid LB medium, in which enzyme expression was induced. Enzyme was extracted by the addition of lysis buffer with a liquid handling robot (Freedom EVO 200, Tecan) and the crude cell extracts were used for enzyme screening. Acceptor screening was performed with the phosphomolybdate assay described above. Donor screening was performed by measuring the release of both glucose and galactose from lactotrehalose (galactose-α-1,1α-glucose), using the GOD-POD assay (see above) and the galactose assay kit from Megazyme, respectively. The clones with the highest activity were sequenced to identify the introduced mutations. The improved enzyme variants were then produced and purified as described for the wild-type enzyme, to allow a more detailed characterization.

RESULTS

Example 1

Characterisation of the Enzyme

By means of sequence alignments (BLAST), we identified a new putative trehalose phosphorylase (TP) in the recently published genome of *Caldanaerobacter subterraneus*, previously known as *Carboxydibrachium pacificum* (Sokolova et al., 2001; Fardeau et al., 2004). To characterize the enzyme, the encoding gene was chemically synthesized using a codon frequency that is optimal for the host organism *E. coli*. The resulting protein contains 783 aminoacids and its sequence is shown by SEQ ID N° 1:

MDMVKKTKKPIYPFEDWTIRETEFSIETNYRNETIFAQANGYMGMRGNFE

EGYSGPDGTSLKGTYINGFYEIHDIIYPEGGYGFAKTGQTMLNVADSKII

ELYVGEEKFDLLKGKIHFYERVLDMKKGCVERKIKWESPSGKIVNVKIKR

IVSLQRQHLAVISFSVEPVNFTGNIKFVSAIDGDVRNITESEDVRVGSNL

KGRVLETVERGTNGFEGWISQKTQKSNLSYTCAMKNELIGTEKYEVLNNV

KEDRVEVAVAFKAEKNRVYILNKFISYYTSKDCDKSETMKLALEEVRRAQ

EDGFCKIEKEQEEFLQSFWEDADVVIEGDKALQQGIRFNMFHLLQSVGRD

GKTNIAAKGLTGEGYEGHYFWDSDIYILPFFLYTKPEIAKALIMYRYNLL

DAARNRAKELGHKGALYPWRTIDGPECSAYFPAGTAQYHINADIVYALKK

-continued

YVEATNDLDFLYDYGCEIVFETARFWEDLGAYIPLKGNKFCINTVTGPDE

YTALVDNNAYTNYMAKMNLEYAYDIANKMKKEVPEKYQKVASKLNLKDEE

IASWKRAANNMYLPYSEELDIIPQDDSFLYKERITVDEIPEDQFPLLLHW

HYLNIYRYQICKQPDVLLLMFLQREKFTIEQLKKNFDYYEPITTHDSSLS

PAIFSILANEIGYTDKAYKYFMMTARMDLDDYNDNVKDGIHAAAMAGSWS

AVVNGFGGMRVYTDELHFTPGLPEGWKMLSFNVKYKGRKINVKLTHEESV

FTLLEGEPIEIFYFDRRVLIKSGENILKGYEEK

The new enzyme was found to be a true trehalose phosphorylase, with a specific activity of 39.8±3.5 U/mg. Activity towards other α-glucobioses such as maltose or kojibiose could not be detected. Its optimal pH and temperature for phosphorolytic activity were found to be 7 and 80° C., respectively. The enzyme is also highly thermostable, retaining 100% of its activity after 1 hour incubation at 65° C. This is crucial for the industrial application of the enzyme, as carbohydrate conversions are typically operated at temperatures of at least 60° C. to avoid microbial contamination.

TABLE 1

Relative activity of TP from *C. pacificum* (at 60° C. and pH 6)

| Acceptor (500 mM) | Relative activity (%) |
|---|---|
| D-Glucose* | 100 |
| D-Xylose | 135 |
| L-Fucose | 109 |
| D-Galactose | 84 |
| L-Arabinose | 80 |
| D-Fucose* | 22 |
| D-Mannose | 14 |
| D-Allose | 5 |
| D-Arabinose | 2 |
| D-Lyxose | 1 |

*30 mM instead of 500 mM

Surprisingly, the enzyme displays high activity towards a variety of monosaccharide acceptors, including D-glucose, D-galactose, D-xylose, L-arabinose and L-fucose (Table 1). This finding allows the exploitation of the enzyme for the production of a wide range of trehalose-analogues. Although the activity of the enzyme on these acceptors is high (as reflected by their respective $k_{cat}$ values), the affinity for other acceptors than glucose (as reflected by their respective $K_m$ values) is relatively low (Table 2). This means that high concentrations of these substrates are required to achieve enzymatic conversion.

TABLE 2

Kinetic parameters of TP from *C. pacificum* (at 60° C. and pH 6)

| Acceptor | $k_{cat}$ (s$^{-1}$) | $K_m$ (mM) | $k_{cat}/K_m$ (s$^{-1}$mM$^{-1}$) |
|---|---|---|---|
| D-Glucose | 59.0 ± 5.4 | 3.5 ± 0.7 | 17 ± 4 |
| D-Xylose | 64.3 ± 4.1 | 20.3 ± 2.9 | 3.2 ± 0.5 |
| L-Arabinose | 51.4 ± 6.1 | 64.8 ± 8.3 | 0.79 ± 0.14 |
| D-Galactose | 54.0 ± 5.7 | 171.5 ± 26.2 | 0.32 ± 0.06 |
| L-fucose | 68.1 ± 3.8 | 183.4 ± 13.8 | 0.371 ± 0.02 |

Example 2

Optimisation of the Acceptor Specificity by Enzyme Engineering

Surprisingly, it was found that the activity of the TP from *C. subterranneus* (Cs) towards alternative acceptors can be optimised by the introduction of mutations. A combination of random and focused mutagenesis has revealed that the residues in the regions 420-480 and 580-670 are the best targets for that purpose. These positions are submitted to site-saturation mutagenesis to identify the amino acid with the strongest effect. For example, saturation of position 442 reveals that the introduction of valine more than doubles the catalytic efficiency ($k_{cat}/K_m$) towards galactose as acceptor, and the same is true for the substitutions K450S and N659Y (Table 3).

Interestingly, a similar result is obtained when the corresponding residues are introduced in the TP from *T. brockii* (Tb). Indeed, mutating positions 440, 448 and 657 (numbering shifts by 2 units) to valine, serine and tyrosine, respectively, also increases this enzyme's efficiency towards galactose as acceptor (Table 3). The influence of other amino acids is less pronounced but can still be significant, as illustrated by mutants A440E, R448F and N657G. The beneficial mutations can be combined to create an enzyme that is even more efficient towards galactose as acceptor. The triple mutant A440V/R448S/N657Y, for example, is about twice as efficient as any of the single mutants (Table 3).

TABLE 3

Kinetic parameters on glucose (Glc) and galactose (Gal) as acceptors (60° C. and pH 6)

| | Glc | | | Gal | | |
|---|---|---|---|---|---|---|
| | $K_m$ | $k_{cat}$ | $k_{cat}/K_m$ | $K_m$ | $k_{cat}$ | $k_{cat}/K_m$ |
| CsTP | | | | | | |
| WT | 3.5 | 59 | 17 | 171.5 | 54 | 0.3 |
| A442V | 2.3 | 67 | 29 | 70.2 | 52 | 0.7 |
| K450S | 2.3 | 62 | 27 | 78.4 | 53 | 0.7 |
| N659Y | 1.2 | 46 | 37 | 46.3 | 51 | 1.1 |
| TbTP | | | | | | |
| WT | 3.8 | 31 | 8 | 98.8 | 33 | 0.3 |
| A440V | 1.9 | 42 | 23 | 45.7 | 33 | 0.7 |
| A440E | 2.3 | 33 | 14 | 68.2 | 23 | 0.3 |
| R448S | 1.5 | 26 | 18 | 33.5 | 32 | 1.0 |
| R448F | 1.2 | 22 | 19 | 45 | 23 | 0.5 |
| N657Y | 3.0 | 54 | 18 | 45.8 | 23 | 0.5 |
| N657G | 2.5 | 43 | 17 | 58.1 | 24 | 0.4 |
| A440V/R448S | 0.7 | 25 | 34 | 30.1 | 39 | 1.3 |
| A440V/R448S/N657Y | 0.4 | 22 | 58 | 31.1 | 55 | 1.8 |

It is important to note that the change in specificity is not limited to galactose as acceptor, but is extended towards other monosaccharides. Introducing the mutation K450N in CsTP, for example, significantly increases the enzyme's specific activity on mannose as acceptor. In turn, mutation P588H increases the affinity towards glucose as acceptor, while the opposite is true for mutation A431T. Through a systematic evaluation of mutant libraries, a wide range of specificities is thus created for the production of trehalose-analogues.

Example 3

Production of Lactotrehalose

A production process for lactotrehalose has been developed with the TP from *C. subterraneus*. Starting from 200 mM β-glucose-1-phosphate and 200 mM galactose, a yield of 75% could be obtained at pH 6 and 60° C. A coupled process using trehalose and galactose as reagents was also undertaken, as this eliminates the need to add β-glucose-1-phosphate as glycosyl donor and thus lowers the costs. Starting from 200 mM trehalose and 400 mM galactose in 30 mM phosphate buffer at pH 7 and 60° C., 120 mM lactotrehalose has been obtained. The product could then conveniently be purified in three simple steps. First, the residual trehalose was degraded to glucose by treatment with *E. coli* trehalase at 37° C. Next, the yeast *Kluyveromyces* was added, which consumes the monosaccharides glucose and galactose through fermentation. And finally, the solution was poured through an anion-exchange column to remove the inorganic and glycosyl phosphate.

Example 4

Optimisation of the Donor Specificity by Enzyme Engineering

Surprisingly, it was found that the activity of the TP from *C. subterranneus* (Cs) towards alternative donors can be optimised by the introduction of mutations. Although other donor substrates besides β-glucose-1-phosphate are not readily available, the enzyme's donor specificity can be conveniently evaluated by examining the phosphorolysis of lactotrehalose. Indeed, this substrate can be positioned in the active site in two different binding modes, i.e. with either the glucosyl moiety or the galactosyl moiety in the donor subsite. In the former case, β-glucose-1-phosphate (βGlc1P) and galactose will be released, while β-galactose-1-phosphate (βGal1P) and glucose will be generated in the latter case.

The wild-type enzyme has nearly no affinity for βGal1P and thus almost exclusively produces β-Glc1P from lactotrehalose. However, through randomization of several positions in the donor subsite, variant enzymes are generated that display a shift in donor specificity (Table 4). The variant L649G, for example, preferentially produced βGal1P since its activity towards βGlc1P was nearly abolished. The subsequent introduction of mutation A693Q selectivity increased the activity towards βGal1P, and this activity could be increased even further by the addition of mutation W371Y. In that way, a triple mutant was created that releases βGal1P from lactotrehalose almost 100 times faster than βGlc1P.

TABLE 4

Specific activity on 100 mM lactotrehalose (pH 7 and 60° C.)

| CsTP | Release of βGal1P (U/mg) | Release of βGlc1P (U/mg) | Ratio βGal1P/βGlc1P |
|---|---|---|---|
| wild-type | 0.13 | 3.0 | 0.04 |
| L649G | 0.22 | 0.09 | 2.6 |
| L649T | 0.34 | 0.43 | 0.8 |
| L649G/A693Q | 1.92 | 0.09 | 22.6 |
| L649G/A693Q/W371Y | 4.70 | 0.05 | 92.8 |

Example 5

Production of β-galactose-1-phosphate

A production process for β-galactose-1-phosphate has been developed with the triple mutant L649G/A693Q/W371Y. Starting from 100 mM lactotrehalose in 500 mM phosphate buffer at pH 7 and 60° C., 60 mM β-galactose-1-phosphate could be produced. The product could then conveniently be purified in two simple steps. First, the remaining inorganic phosphate was precipitated as struvite by the addition of magnesium acetate and ammonia. Then, the glycosyl phosphate was separated from the neutral sugars lactotrehalose and glucose by means of anion-exchange chromatography. The final product was about 98% pure, containing only trace amounts of β-glucose-1-phosphate as contaminant.

Example 6

Production of Other Glycosyl Phosphates

The anomeric phosphorylation of monosaccharides is one of the most efficient strategies to increase their reactivity. Indeed, glycosyl phosphates are widely used as powerful donor substrates for both chemical and enzymatic glycosylation reactions (Plante et al., 1999). Such compounds have traditionally been synthesized by means of conventional chemical catalysis, and several of these procedures have been patented (e.g. EP0553297). The enzymatic phosphorylation of carbohydrates is, however, considerably more efficient and also more environmentally-friendly. The only downside is that sugar kinases require ATP as co-substrate, which is too expensive for industrial application. Nevertheless, efforts have been made to broaden the specificity of kinases towards various rare sugars (WO2005056786).

Figure 1:
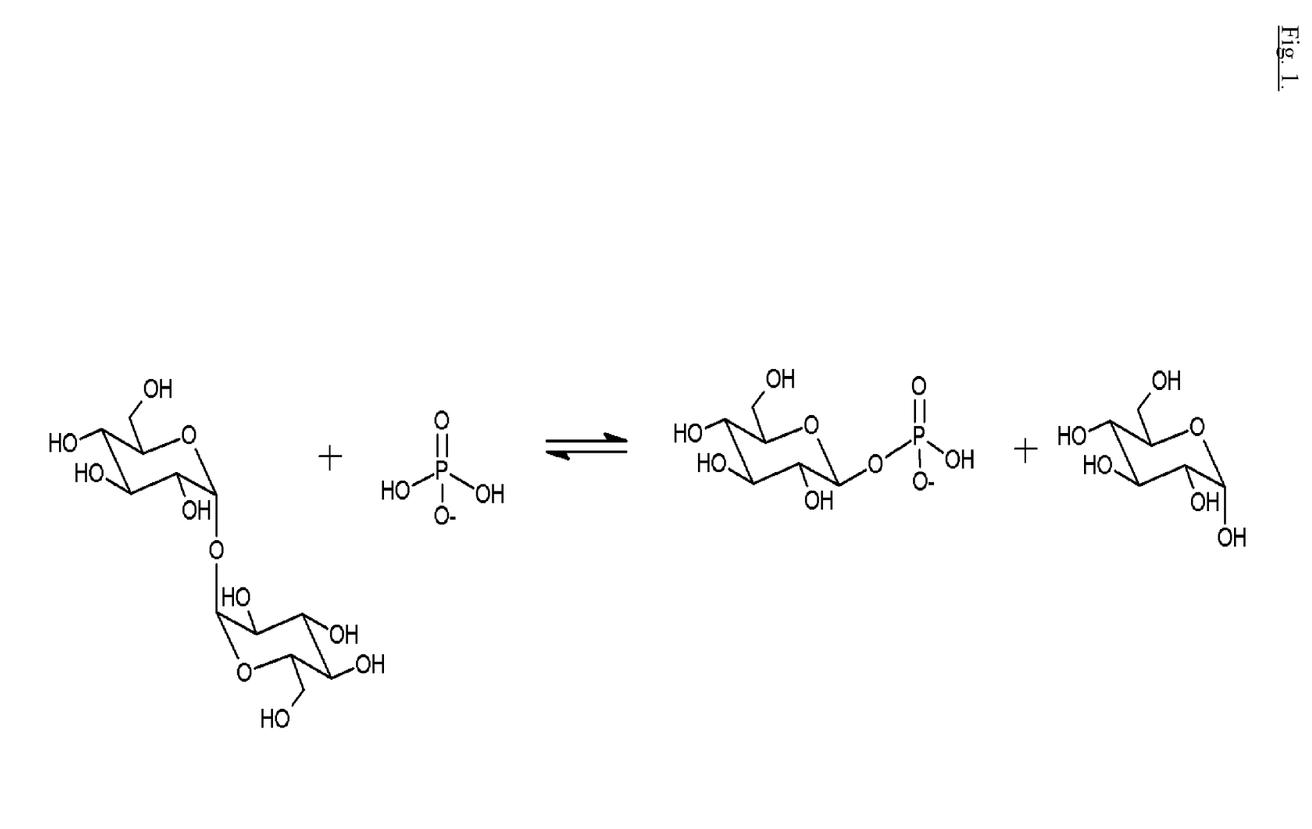
FIG. 1. The phosphorolytic degradation of trehalose catalyzed by wild-type trehalose phosphorylase.
Figure 2:
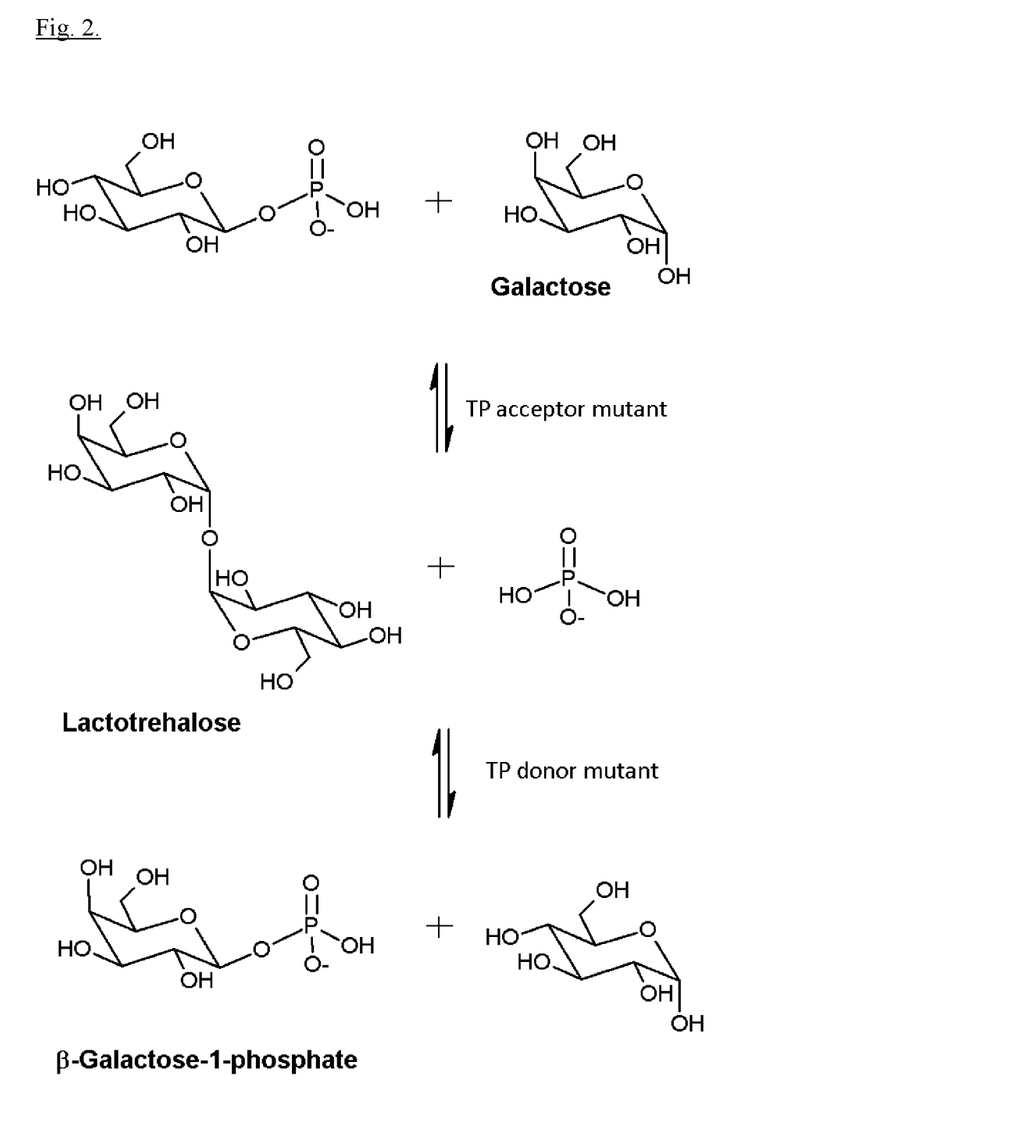
FIG. 2. The activity of mutant trehalose phosphorylases (TP) on galactose as acceptor and/or on lactotrehalose as substrate, resulting in the production of β-galactose-1-phosphate.

Here, an alternative strategy for the enzymatic phosphorylation of monosaccharides is disclosed that is not only cheaper but also universally applicable. Indeed, through the engineering of TP, any monosaccharide can be phosphorylated in a two-step process that only requires inorganic phosphate as co-substrate (FIG. 2). In a first step, the monosaccharide enters the process as acceptor substrate for a mutant TP with optimized acceptor specificity, generating the corresponding trehalose-analogue as product. Because of the non-reducing nature of such disaccharides, the starting compound can then be positioned in the donor subsite of a mutant TP with optimized donor specificity, and exit the process as the corresponding glycosyl phosphate. The conversion of galactose to β-galactose-1-phosphate is described above, but this strategy is extended to other monosaccharides such as D-xylose, L-arabinose and L-fucose.

REFERENCES

Aerts D, Verhaeghe T, De Mey M, Desmet T and Soetaert W (2010) A constitutive expression system for high-throughput screening. *Eng. Life Sci.* 11:10-19

Aisaka K, Masuda-Kato T, Chikamune T, Kamitori K, Uosaki Y, Saito Y (2000) Enzymatic synthesis of novel disaccharides using disaccharide phosphorylases. *J Biosci Bioeng*, 90(2):208-213.

Belocopitow E, Marechal L R, Gros E G (1971) Enzymic synthesis of 6-deoxy-α-D-glucopyranosyl α-D-glucopyranoside and α-D-xylopyranosyl α-D-glucopyranoside. Carbohydr Res, 19(2):268-271

Chaen H, Nakada T, Nishimoto T, Kuroda N, Fukuda S, Sugimoto T, Kurimoto M and Tsujisaka Y (1999) Purification and characterization of thermostable trehalose phosphorylase from *Thermoanaerobacter brockii. Journal of Applied Glycoscience*, 46, 399-405.

Chaen H, Nakada T, Mukai N, Nishimoto T (2001) Efficient enzymatic synthesis of disaccharide α-D-galactosyl α-D-glucoside by trehalose phosphorylase from *Thermoanaerobacter brockii. Journal of Applied Glycoscience*, 48, 135-137

Fardeau M, Salinas, M B, L'Haridon S, Jeanthon C, Verhé F, Cayol J, Patel B K C, Garcia J, Ollivier B (2004) Isolation from oil reservoirs of novel thermophilic anaerobes phylogenetically related to *T. subterraneus*: reassignment of *Thermoanaerobacter yonseiensis*, *Thermoanaerobacter tengcongensis* and *Carboxydibrachium pacificum* to *Caldanaerobacter subterraneus* gen. nov., sp. nov., comb nov as four novel species. *International Journal of Systematic and Evolutionary Microbiology*. 54, 467-74.

Gawronski J D, and Benson D R (2004) Microtiter assay for glutamine synthetase biosynthetic activity using inorganic phosphate detection. *Analytical Biochemistry*, 327, 114-18.

Higashiyama T (2002) Novel functions and applications of trehalose. Pure and Applied Chemistry, 74, 1263-1269.

Kim H M, Chang Y K, Ryu S I, Moon S G and Lee S B (2007) Enzymatic synthesis of a galactose-containing trehalose analogue disaccharide by *Pyrococcus horikoshii* trehalose-synthesizing glycosyltransferase: Inhibitory effects on several disaccharidase activities. *Journal of Molecular Catalysis B*, 49, 98-103.

Lee C K (1976) Synthesis of alpha-D-glucopyranosyl alpha-D-galactopyranoside. Carbohydr Res, 50(1):152-157.

Maruta K, Nakada T, Kubota M, Chaen H, Sugimoto T, Kurimoto M, Tsujisaka Y (1995) Formation of trehalose from maltooligosaccharides by a novel enzymatic system. *Biosci. Biotechnol. Biochem.* 59, 1829-1834

Maruta K, Mukai K, Yamashita H, Kubota M, Chaen H, Fukuda S, Kurimoto M (2002) Gene encoding a trehalose phosphorylase from *Thermoanaerobacter brockii* ATCC 35047. *Biosci. Biotechnol. Biochem.* 66, 1976-1980.

Maruta K, Watanabe H, Nishimoto T, Kubota M, Chaen H, Fukuda S, Kurimoto M, Tsujisaka Y (2006) Acceptor specificity of trehalose phosphorylase from *Thermoanaerobacter brockii*: production of novel nonreducing trisaccharide, 6-O-alpha-D-galactopyranosyl trehalose. *J. Biosci. Bioengin.* 101:385-390

Plante O J, Andrade R B and Seeberger P H (1999) Synthesis and Use of Glycosyl Phosphates as Glycosyl Donors. *Org. Lett.*, 1(2), 211-214

Pratt M R, Leigh C D, Bertozzi C R (2003) Formation of 1,1-α,α-glycosidic bonds by intramolecular aglycone delivery. *Organic Letters*, 5, 3185-3188.

Sanchis J et al. (2008) Improved PCR method for the creation of saturation mutagenesis libraries in directed evolution: application to difficult-to-amplify templates. Applied Microbiol Biotechnol. 81, 387-397.

Sokolova T G, González J M, Kostrikina N A, Chernyh N A, Tourova T P, Kato C, Bonch-Osmolovskaya E A, Robb F T (2001) Carboxydobrachium pacificum gen. nov., sp. nov., a new anaerobic, thermophilic CO-utilizing marine bacterium from Okinawa Trough. *International Journal of Systematic and Evolutionary Microbiology*. 51, 141-49.

Werner W, Rey H G, and Wielinge H (1970) Properties of a new chromogen for determination of glucose in blood according to GOD/POD-method. *Z. Anal. Chem. Freseniu*, 252, 224.

Yamamoto T, Yamashita H, Mukai K, Watanabe H, Kubota M, Chaen H, Fukuda S (2006) Construction and characterization of chimeric enzymes of kojibiose phosphorylase and trehalose phosphorylase from *Thermoanaerobacter brockii*. *Carbohydrate Research* 341: 2350-2359

Youssef R H, Bassily R W, Asaad A N, el-Sokkary R I, Nashed M A (1995) A facile synthesis of alpha-D-galactopyranosyl-(1→1)-alpha-D-galactopyranoside and its analogues. Carbohydr Res. 22; 277(2):347-351.

---

The invention claimed is:

1. A mutated trehalose phosphorylase comprising the amino acid sequence of SEQ ID NO: 1, except for a mutation in one or more of amino acid positions 371, 442, 450, 649, 659, or 693, and wherein said mutated trehalose phosphorylase has an increased catalytic efficiency towards its acceptor or donor substrate compared to the corresponding wild-type trehalose phosphorylase.

2. The mutated trehalose phosphorylase of claim 1, wherein said mutation is at amino acid positions 371, 442, 450, 649, 659, and 693 of SEQ ID NO: 1.

3. The mutated trehalose phosphorylase of claim 1, wherein said mutation is at amino acid positions 442, 450, or 659 of SEQ ID NO: 1.

4. The mutated trehalose phosphorylase of claim 1, wherein said mutated trehalose phosphorylase is recombinantly expressed in a host cell.

5. A method to produce trehalose-analogues-comprising:
contacting the mutated trehalose phosphorylase of claim 1 with β-glucose-1-phosphate and a monosaccharide,
glycosylating said monosaccharide with β-glucose to obtain a trehalose-analogue, and
purifying said trehalose-analogue, wherein said trehalose-analogue is selected from the group consisting of trehalose, lactotrehalose, glycosylarabinose, glycosylxylose and glycosylfucose.

6. A method to produce trehalose analogues comprising:
contacting the mutated trehalose phosphorylase of claim 1 with trehalose and a monosaccharide in phosphate buffer,
glycosylating said monosaccharide with said trehalose to obtain a trehalose-analogue, and purifying said trehalose-analogue, wherein said trehalose-analogue is selected from the group consisting of lactotrehalose, glycosylarabinose, glycosylxylose and glycosylfucose.

7. The method of claim 5, wherein said monosaccharide is selected from the group consisting of D-glucose, D-xylose, L-arabinose, L-fucose, and D-galactose.

8. A method to produce β-galactose-1-phosphate comprising:
   contacting the mutant trehalose phosphorylase of claim 1 with lactotrehalose in phosphate buffer, to produce β-galactose-1-phosphate, and
   purifying said β-galactose-1-phosphate.

9. The method of claim 6, wherein said monosaccharide is selected from the group consisting of D-glucose, D-xylose, L-arabinose, L-fucose, and D-galactose.

* * * * *

SEQUENCE LISTING

```
<160> NUMBER OF SEQ ID NOS: 3

<210> SEQ ID NO 1
<211> LENGTH: 783
<212> TYPE: PRT
<213> ORGANISM: Caldanaerobacter subterraneus

<400> SEQUENCE: 1

Met Asp Met Val Lys Lys Thr Lys Lys Pro Ile Tyr Pro Phe Glu Asp
1               5                   10                  15

Trp Thr Ile Arg Glu Thr Glu Phe Ser Ile Glu Thr Asn Tyr Arg Asn
            20                  25                  30

Glu Thr Ile Phe Ala Gln Ala Asn Gly Tyr Met Gly Met Arg Gly Asn
        35                  40                  45

Phe Glu Glu Gly Tyr Ser Gly Pro Asp Gly Thr Ser Leu Lys Gly Thr
    50                  55                  60

Tyr Ile Asn Gly Phe Tyr Glu Ile His Asp Ile Ile Tyr Pro Glu Gly
65                  70                  75                  80

Gly Tyr Gly Phe Ala Lys Thr Gly Gln Thr Met Leu Asn Val Ala Asp
                85                  90                  95

Ser Lys Ile Ile Glu Leu Tyr Val Gly Glu Glu Lys Phe Asp Leu Leu
            100                 105                 110

Lys Gly Lys Ile His Phe Tyr Glu Arg Val Leu Asp Met Lys Lys Gly
        115                 120                 125

Cys Val Glu Arg Lys Ile Lys Trp Glu Ser Pro Ser Gly Lys Ile Val
    130                 135                 140
```

```
Asn Val Lys Ile Lys Arg Ile Val Ser Leu Gln Arg Gln His Leu Ala
145                 150                 155                 160

Val Ile Ser Phe Ser Val Glu Pro Val Asn Phe Thr Gly Asn Ile Lys
            165                 170                 175

Phe Val Ser Ala Ile Asp Gly Asp Val Arg Asn Ile Thr Glu Ser Glu
            180                 185                 190

Asp Val Arg Val Gly Ser Asn Leu Lys Gly Arg Val Leu Glu Thr Val
            195                 200                 205

Glu Arg Gly Thr Asn Gly Phe Glu Gly Trp Ile Ser Gln Lys Thr Gln
            210                 215                 220

Lys Ser Asn Leu Ser Tyr Thr Cys Ala Met Lys Asn Glu Leu Ile Gly
225                 230                 235                 240

Thr Glu Lys Tyr Glu Val Leu Asn Asn Val Lys Glu Asp Arg Val Glu
            245                 250                 255

Val Ala Val Ala Phe Lys Ala Glu Lys Asn Arg Val Tyr Ile Leu Asn
            260                 265                 270

Lys Phe Ile Ser Tyr Tyr Thr Ser Lys Asp Cys Asp Lys Ser Glu Thr
            275                 280                 285

Met Lys Leu Ala Leu Glu Glu Val Arg Arg Ala Gln Glu Asp Gly Phe
290                 295                 300

Cys Lys Ile Glu Lys Glu Gln Glu Glu Phe Leu Gln Ser Phe Trp Glu
305                 310                 315                 320

Asp Ala Asp Val Val Ile Glu Gly Asp Lys Ala Leu Gln Gln Gly Ile
            325                 330                 335

Arg Phe Asn Met Phe His Leu Leu Gln Ser Val Gly Arg Asp Gly Lys
            340                 345                 350

Thr Asn Ile Ala Ala Lys Gly Leu Thr Gly Glu Gly Tyr Glu Gly His
            355                 360                 365

Tyr Phe Trp Asp Ser Asp Ile Tyr Ile Leu Pro Phe Phe Leu Tyr Thr
            370                 375                 380

Lys Pro Glu Ile Ala Lys Ala Leu Ile Met Tyr Arg Tyr Asn Leu Leu
385                 390                 395                 400

Asp Ala Ala Arg Asn Arg Ala Lys Glu Leu Gly His Lys Gly Ala Leu
            405                 410                 415

Tyr Pro Trp Arg Thr Ile Asp Gly Pro Glu Cys Ser Ala Tyr Phe Pro
            420                 425                 430

Ala Gly Thr Ala Gln Tyr His Ile Asn Ala Asp Ile Val Tyr Ala Leu
            435                 440                 445

Lys Lys Tyr Val Glu Ala Thr Asn Asp Leu Asp Phe Leu Tyr Asp Tyr
450                 455                 460

Gly Cys Glu Ile Val Phe Glu Thr Ala Arg Phe Trp Glu Asp Leu Gly
465                 470                 475                 480

Ala Tyr Ile Pro Leu Lys Gly Asn Lys Phe Cys Ile Asn Thr Val Thr
            485                 490                 495

Gly Pro Asp Glu Tyr Thr Ala Leu Val Asp Asn Ala Tyr Thr Asn
            500                 505                 510

Tyr Met Ala Lys Met Asn Leu Glu Tyr Ala Tyr Asp Ile Ala Asn Lys
            515                 520                 525

Met Lys Lys Glu Val Pro Glu Lys Tyr Gln Lys Val Ala Ser Lys Leu
            530                 535                 540

Asn Leu Lys Asp Glu Glu Ile Ala Ser Trp Lys Arg Ala Ala Asn Asn
545                 550                 555                 560

Met Tyr Leu Pro Tyr Ser Glu Glu Leu Asp Ile Ile Pro Gln Asp Asp
```

|   |   |   |   |   |   |   |   |   |   |   |   |
|---|---|---|---|---|---|---|---|---|---|---|---|
|   |   |   | 565 |   |   | 570 |   |   | 575 |   |   |
| Ser | Phe | Leu | Tyr | Lys | Glu | Arg | Ile | Thr | Val | Asp | Glu | Ile | Pro | Glu | Asp |
|   |   |   | 580 |   |   |   |   | 585 |   |   |   |   | 590 |   |   |

Ser Phe Leu Tyr Lys Glu Arg Ile Thr Val Asp Glu Ile Pro Glu Asp
                580                585                590

Gln Phe Pro Leu Leu Leu His Trp His Tyr Leu Asn Ile Tyr Arg Tyr
            595                600                605

Gln Ile Cys Lys Gln Pro Asp Val Leu Leu Leu Met Phe Leu Gln Arg
        610                615                620

Glu Lys Phe Thr Ile Glu Gln Leu Lys Lys Asn Phe Asp Tyr Tyr Glu
625                630                635                640

Pro Ile Thr Thr His Asp Ser Ser Leu Ser Pro Ala Ile Phe Ser Ile
                645                650                655

Leu Ala Asn Glu Ile Gly Tyr Thr Asp Lys Ala Tyr Lys Tyr Phe Met
            660                665                670

Met Thr Ala Arg Met Asp Leu Asp Asp Tyr Asn Asp Asn Val Lys Asp
                675                680                685

Gly Ile His Ala Ala Ala Met Ala Gly Ser Trp Ser Ala Val Val Asn
            690                695                700

Gly Phe Gly Gly Met Arg Val Tyr Thr Asp Glu Leu His Phe Thr Pro
705                710                715                720

Gly Leu Pro Glu Gly Trp Lys Met Leu Ser Phe Asn Val Lys Tyr Lys
                725                730                735

Gly Arg Lys Ile Asn Val Lys Leu Thr His Glu Glu Ser Val Phe Thr
            740                745                750

Leu Leu Glu Gly Glu Pro Ile Glu Ile Phe Tyr Phe Asp Arg Arg Val
            755                760                765

Leu Ile Lys Ser Gly Glu Asn Ile Leu Lys Gly Tyr Glu Glu Lys
            770                775                780

```
<210> SEQ ID NO 2
<211> LENGTH: 2352
<212> TYPE: DNA
<213> ORGANISM: Caldanaerobacter subterraneus

<400> SEQUENCE: 2
atggatatgg tgaaaaagac gaagaagccc atttacccct ttgaagattg gacaataagg      60
gagacagagt ttagcataga aacaaactat agaaatgaga caattttgc tcaggcgaat     120 ggatatatgg gaatgagagg aaattttgaa gaagggtatt caggacctga cggtacttcc     180
ttaaaaggga cttatattaa tgggttttat gaaatacacg atatcatcta ccctgaaggg     240
ggatacggtt tgcgaaaac agggcagacc atgttaaatg tggctgacag caaaataata     300
gaattgtacg taggagaaga aaaatttgac cttttaaaag gtaaaatcca cttttatgaa     360
agagtacttg atatgaaaaa aggttgtgta gaaagaaaga taagtgggga gtctccttca     420
ggaaagattg taaatgtaaa aataaagaga attgtttcat tgcaaaggca acatttagca     480
gtaatttctt tttctgtaga acctgttaat tttacgggaa atataaaatt tgtatctgct     540
attgatggag atgtgaggaa cattactgag agcgaagatg taagagtggg ttcaaatctg     600
aaggggagag ttttagagac cgtcgaaaga ggaacaaatg gctttgaggg atggatttct     660
caaaaaacac aaaaaagcaa cctttcatat acttgcgcaa tgaaaaatga actcattggg     720
acagaaaaat acgaggtttt gaacaacgta aagaagata gggtagaggt tgcagtagct     780 tttaagctg agaagaatag ggtatacatt ctgaataaat ttatatctta ttatacctca     840
aaagattgcg acaaaagtga aacaatgaaa ttggccttag aagaagtgag aagagcacaa     900
```

```
gaagatggat tttgcaaaat agaaaaagag caggaagaat ttttgcaatc tttctgggaa    960
gatgccgatg tagtaataga aggagataag gctctgcagc agggtataag atttaatatg   1020
tttcaccttt tgcagtctgt cggtagagac ggaaaaacta atattgcggc aaagggactt   1080
actggggaag ggtatgaagg ccattacttt tgggattctg atatctatat attgcctttt   1140
ttcctttaca cgaagccaga aattgcaaaa gctttaataa tgtatagata taacctctta   1200
gatgctgcga gaaatagggc taaagagttg gggcataaag gagctttata ccctggagg    1260
acaattgatg gacctgaatg ttctgcatac tttcctgctg gaactgctca atatcacata   1320
aatgctgata tagtttatgc tttaaaaaag tatgtggagg ccacgaatga tttggatttt   1380
ctctatgact acggctgtga aatagtattt gaaactgcaa ggttttggga agatttagga   1440
gcatatattc ctcttaaagg aaataaattc tgtataaaca ctgtcactgg tcctgatgag   1500
tatacggcat tggttgataa taacgcatat acaaattata tggcaaaaat gaatttggaa   1560
tacgccatg atattgcaaa caaaatgaaa aaggaagtgc ctgaaaagta tcaaaaggtc    1620
gcttcaaaac taaatctaaa ggatgaagag attgcttcgt ggaaaagggc agctaacaat   1680
atgtaccttc cttactcgga agagcttgat attataccac aggatgacag ttttttgtat   1740
aaagaaagga taacagtgga tgaaataccg gaagatcaat ttccgttatt gcttcactgg   1800
cactacctca acatttacag gtatcagatc tgcaaacagc ctgatgtgtt gcttttgatg   1860
tttttacaga gagaaaaatt tactatagaa cagcttaaaa agaattttga ttattatgaa   1920
cctattacta ctcacgactc ttccctgtcg ccagcaatat ttagtatact tgccaatgaa   1980
atagggtata ctgacaaagc ttataaatac tttatgatga ctgcaaggat ggacttggat   2040
gattacaatg acaatgtaaa agatggaatt catgctgcag caatggcagg tcctggagt    2100
gccgttgtaa atggttttgg aggaatgaga gtttatacag atgaactgca ctttactcca   2160
ggactgcctg aggggtggaa gatgctctct tttaatgtaa agtacaaagg gaggaagata   2220
aatgtaaaat taactcatga agaatcagta tttacccttt tggaaggaga acctatagaa   2280
attttctatt ttgacagaag agtgttaata aagtcaggag aaaatatact aaaagggtat   2340
gaggagaagt ga                                                       2352
```

<210> SEQ ID NO 3
<211> LENGTH: 2352
<212> TYPE: DNA
<213> ORGANISM: Caldanaerobacter subterraneus

<400> SEQUENCE: 3

```
atggacatgg ttaaaaaaac caaaaaaccg atctacccgt tcgaagactg gaccatccgt     60
gaaaccgaat tctctatcga aaccaactac cgtaacgaaa ccatcttcgc tcaggctaac    120
ggttacatgg gtatgcgtgg taacttcgaa gaaggttact ctggtccgga cggtacctct    180
ctgaaaggta cctacatcaa cggttttctac gaaatccacg acatcatcta cccggaaggt    240
ggttacggtt tcgctaaaac cggtcagacc atgctgaacg ttgctgactc taaaatcatc    300
gaactgtacg ttggtgaaga aaaattcgac ctgctgaaag gtaaaatcca cttctacgaa    360
cgtgttctgg acatgaaaaa aggttgcgtt gaacgtaaaa tcaaatggga atctccgtct    420
ggtaaaatcg ttaacgttaa atcaaacgt atcgtttctc tgcagcgtca gcacctggct     480
gttatctctt tctctgttga accggttaac ttcaccggta acatcaaatt cgtttctgct    540
atcgacggta cgttcgtaa catcaccgaa tctgaagacg ttcgtgttgg ttctaacctg    600
aaaggtcgtg ttctggaaac cgttgaacgt ggtaccaacg gtttcgaagg ttggatctct    660
```

```
cagaaaaccc agaaatctaa cctgtcttac acctgcgcta tgaaaaacga actgatcggt      720
accgaaaaat acgaagttct gaacaacgtt aaagaagacc gtgttgaagt tgctgttgct      780
ttcaaagctg aaaaaaaccg tgtttacatc ctgaacaaat tcatctctta ctacacctct      840
aaagactgcg acaaatctga aaccatgaaa ctggctctgg aagaagttcg tcgtgctcag      900
gaagacggtt tctgcaaaat cgaaaagaa caggaagaat tcctgcagtc tttctgggaa       960
gacgctgacg ttgttatcga aggtgacaaa gctctgcagc agggtatccg tttcaacatg     1020
ttccacctgc tgcagtctgt tggtcgtgac ggtaaaacca acatcgctgc taaaggtctg     1080
accggtgaag gttacgaagg tcactacttc tgggactctg acatctacat cctgccgttc     1140
ttcctgtaca ccaaaccgga aatcgctaaa gctctgatca tgtaccgtta caacctgctg     1200
gacgctgctc gtaaccgtgc taaagaactg ggtcacaaag tgctctgta cccgtggcgt      1260 accatcgacg gtccggaatg ctctgcttac ttcccggctg gtaccgctca gtaccacatc     1320
aacgctgaca tcgtttacgc tctgaaaaaa tacgttgaag ctaccaacga cctggacttc     1380
ctgtacgact acggttgcga aatcgttttc gaaaccgctc gtttctggga agacctgggt     1440
gcttacatcc cgctgaaagg taacaaattc tgcatcaaca ccgttaccgg tccggacgaa     1500
tacaccgctc tggttgacaa caacgcttac accaactaca tggctaaaat gaacctggaa     1560
tacgcttacg acatcgctaa caaatgaaa aagaagttc cggaaaaata ccagaaagtt       1620
gcttctaaac tgaacctgaa agacgaagaa atcgcttctt ggaaacgtgc tgctaacaac     1680
atgtacctgc cgtactctga agaactggac atcatcccgc aggacgactc tttcctgtac     1740
aaagaacgta tcaccgttga cgaaatcccg gaagaccagt tcccgctgct gctgcactgg     1800
cactacctga acatctaccg ttaccagatc tgcaaacagc cggacgttct gctgctgatg     1860
ttcctgcagc gtgaaaaatt caccatcgaa cagctgaaaa aaaacttcga ctactacgaa     1920
ccgatcacca cccacgactc ttctctgtct ccggctatct tctctatcct ggctaacgaa     1980
atcggttaca ccgacaaagc ttacaaatac ttcatgatga ccgctcgtat ggacctggac     2040
gactacaacg acaacgttaa agacggtatc cacgctgctg ctatggctgg ttcttggtct     2100
gctgttgtta acggtttcgg tggtatgcgt gtttacaccg acgaactgca cttcaccccg     2160
ggtctgccgg aaggttggaa aatgctgtct ttcaacgtta aatacaaagg tcgtaaaatc     2220
aacgttaaac tgacccacga agaatctgtt ttcaccctgc tggaaggtga accgatcgaa     2280
atcttctact tcgaccgtcg tgttctgatc aaatctggtg aaaacatcct gaaaggttac     2340
gaagaaaaat aa                                                         2352
```